Figure 1:
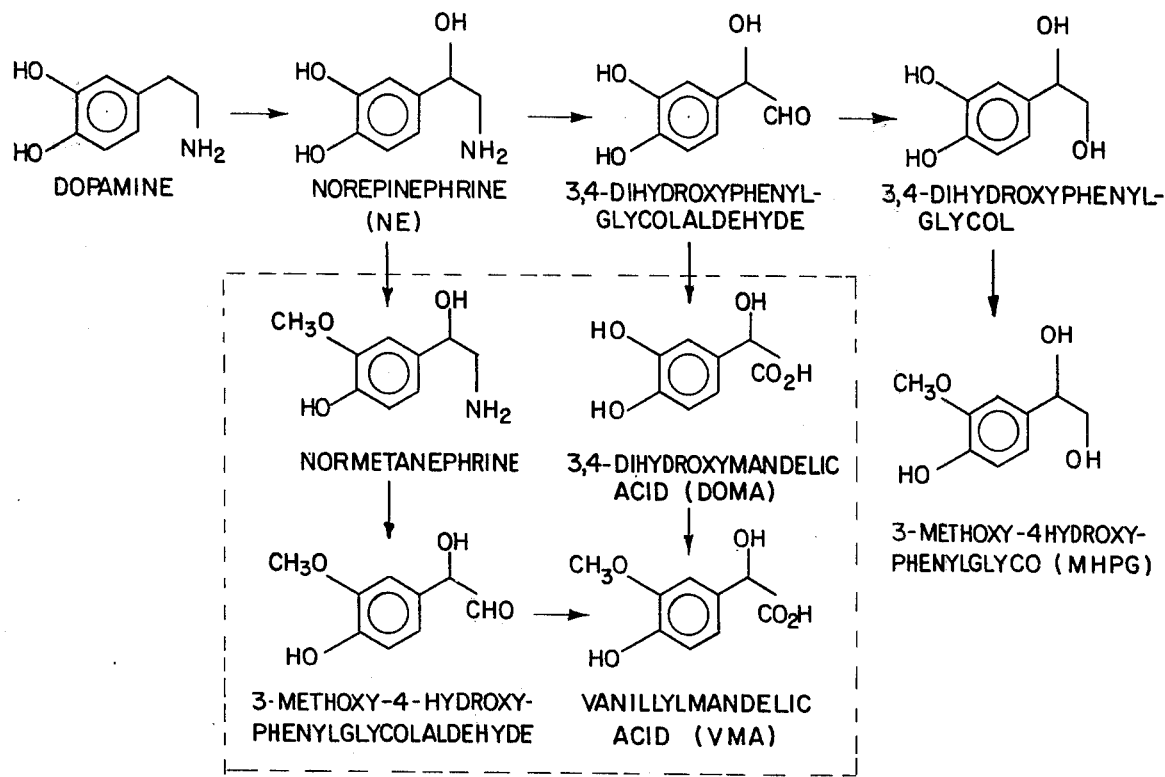

United States Patent [19]

Kobrinsky

[11] 4,259,947
[45] Apr. 7, 1981

[54] METHOD FOR MEASUREMENT OF THE NEUROCHEMISTRY OF THE BRAIN

[76] Inventor: Peter C. Kobrinsky, 724 Calabria Dr., Santa Barbara, Calif. 93105

[21] Appl. No.: 93,760

[22] Filed: Nov. 13, 1979

[51] Int. Cl.$^3$ ............................................. A61B 19/00
[52] U.S. Cl. ......................................... 128/1 R; 424/9
[58] Field of Search ................... 128/1 R, 630; 424/1, 424/2, 9

[56] References Cited

PUBLICATIONS

"The Biochemical Basis of Neuropharmacology", Cooper et al., 3rd Edition, Oxford Press.
"The Pharmacology Basis of Therapeutics", Goodman et al., 5th Ed.
"The Metabolism of Circulating Norepinephrine by Human Subjects", J. of Pharmacology and Exp. Therapeutics, Maas et al., 1971.
"Differentially Labeling of Origins of Urinary Catecholamine by Dopamine C$^{14}$", 28 Trans. Assoc. Am. Physician 256, Ebert et al., 1975.
Estimation of the Contribution of Peripheral and Central Noradonergic Neurones to Urinary 3–Methoxy–4–Hydroxy–Phenylglycol in the Rat, 13 Neuropharmacology, Karoum et al., 1974, p. 165.
"Toward a Biochemical Classification of Depressive Disorders", 35th Arch. Gen. Psychiatry, 1427 (1978), Schildkraut et al.
"Current Status of the Catecholamine Hypothesis of the Affective Disorders", Psychopharmacology, Lipton et al., 1978.

Primary Examiner—Robert W. Michell
Assistant Examiner—Thomas Wallen
Attorney, Agent, or Firm—Jenkins, Coffey, Hyland, Badger & Conard

[57] ABSTRACT

A method for determining the norepinephrine activity of a human brain may provide information useful to the diagnosis and treatment of affective disorders. In such a method, the norepinephrine metabolite, 3-methoxy-4-hydroxyphenylglycol, produced by the brain can be measured separately from that produced by the peripheral nervous system. A sample is taken for measuring the total body levels of the norepinephrine metabolites, 3-methoxy-4-hydroxyphenylglycol and vanillylmandelic acid. A dose of isotopically labelled norepinephrine is administered to the body of the subject. Subsequent to the administration of the labelled norepinephrine, samples are collected for measuring the total body levels of isotopically labelled metabolites, 3-methoxy-4-hydroxyphenylglycol and vanillylmandelic acid. Since vanillylmandelic acid is metabolized from norepinephrine substantially entirely in the peripheral nervous system, the brain's contribution of 3-methoxy-4-hydroxyphenylglycol can be determined.

18 Claims, 2 Drawing Figures

METHOD FOR MEASUREMENT OF THE NEUROCHEMISTRY OF THE BRAIN

In recent years it has become apparent that norepinephrine (NE) is important in the chemistry of neural activity in humans as well as other animals. Abnormal levels of certain biochemical compounds, including norepinephrine, its precursors and metabolites, have been correlated with some psychological disorders. J. Schildkraut, et al, in *Toward a Biochemical Classification of Depressive Disorders*, ±Arch. Gen. Psychiatry 1427 (1978), found the levels of urinary MHPG (3-methoxy-4-hydroxyphenylglycol, a metabolite of NE) of patients with bipolar manic-depressive depressions to be considerably lower than similar patients with unipolar nonendogenous depressions, although there were no significant differences in age, sex, depression ratings, urine volume, or creatine excretion between the groups. Several other groups of patients showed similar correlative findings, suggesting that urinary MHPG levels may be useful in differentiating subtypes of affective disorders.

A paper by J. Schildkraut, *Current Status of the Catecholamine Hypothesis of Affective Disorders* in Psychopharmacology: A Generation of Progress 1223 (M. Lipton, et al, ed. 1978), provides a review of the literature concerning the importance of deficiencies of catecholamines, particularly norepinephrine in depressive disorders.

Norepinephrine (NE) is produced by the body in both the brain and the peripheral nervous system (periphery), but the blood/brain barrier prevents any significant intermixing of the NE from these two sources. The measurement of NE is usually not direct, but rather is accomplished by measurement of one of its metabolites, MHPG (3-methoxy-4-hydroxyphenylglycol). However, MHPG is excreted from the brain and the periphery and does penetrate the blood/brain barrier and a measurement of MHPG from the blood or urine reflects the MHPG level that results from the NE activity of both the brain and peripheral nervous system (periphery). A second metabolite of NE, vanillylmandelic acid (VMA) is produced from NE by the peripheral nervous system, but very little is produced by the brain.

With the apparent importance of NE activity in the brain, it would seem desirable to be able to determine the activity by determining the MHPG produced by the brain from NE separately from that produced by the peripheral nervous system. However, prior efforts at differentiating between brain and peripheral MHPG have not been satisfactory.

Massive and continual doses of labelled NE would result in most of the peripheral NE being labelled, and resultantly, most of the MHPG produced by the periphery would be labelled. The problem with this approach is that large doses of NE will disturb the body's natural balances and distort the diagnosis.

F. Karoum, et al, in *Estimation of the Contribution of Peripheral and Central Noradonergic Neurones to Urinary 3-Methoxy-4-Hydroxyphenylglycol in the Rat*, 13 Neuropharmacology 165 (1974), used debrisoquine to inhibit the monoamine oxidase (MAO) metabolism of NE to MHPG. This method also has the undesirable effect of disturbing the body's natural biochemical state, and is unsuitable for human use.

Recognizing the importance of NE activity in the diagnosis of affective disorders, it is desirable to have available an accurate method for determining these levels. Accordingly, this invention is directed to a cost-effective, accurate method for determining the NE activity of the brain of humans. In such a method, MHPG produced by the brain NE activity is determined separately from that attributable to the peripheral nervous system. This invention thus provides a method for determining the neurochemical activity of the brain without disturbing the body's normal chemical equilibrium.

Figure 2:
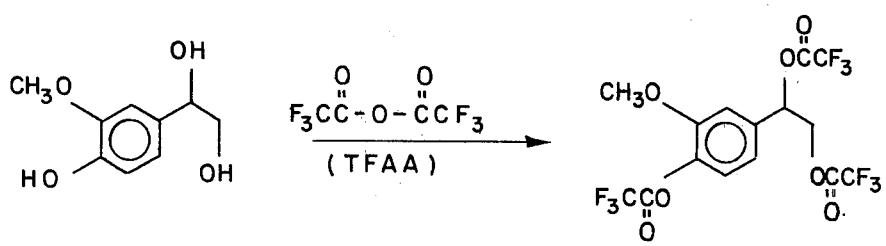

In the drawings:

FIG. 1 is a representation of a portion of the biochemical pathways of the human body; and FIG. 2 is a representation of the reaction of MHPG with TFAA.

Referring to FIG. 1, norepinephrine (NE) is metabolized through two illustrated pathways to vanillylmandelic acid (VMA) and through one illustrated pathway to 3-methoxy-4-hydroxyphenylglycol (MHPG). Importantly, this illustration is only partial. The neurochemistry of man is only partially understood and there are other reaction pathways (not shown) which interact with the compounds diagrammed in FIG. 1.

The portion of the reaction pathway of FIG. 1 outside of the dotted line (NE→MHPG) takes place in both the brain and the peripheral nervous system hereafter referred to as the periphery, but the reactions within the dotted line (NE→VMA) exist to any appreciable extent only in the periphery.

The present invention solves the problem of differentiating brain/periphery produced MHPG by a method involving the measurement of MHPG and VMA levels in the body before and after the administration of isotope labelled NE.

First, a measurement of the levels of MHPG and VMA in either the blood or urine will be made over a period of, for example, twenty-four hours. Secondly, a measured amount of deuterated NE ($NE_d$) will be administered intravenously. This $NE_d$ will not cross the blood-brain barrier, and will be present only in the periphery. Thirdly, blood or urine samples will again be taken and analyzed for MHPG and VMA levels, this time measuring only deuterated MHPG ($MHPG_d$) and deuterated VMA ($VMA_d$). The raw data is then used in the equation:

$$MHPG_{(brain)} = MHPG_{(total)} - \left[ VMA_{(total)} \left( \frac{MHPG_d}{VMA_d} \right) \right] \quad [1.]$$

where the figures designated "total" are those taken before the administration of deuterated NE and those designated "d" are the deuterated metabolites resulting from the NE injection. $MHPG_{brain}$ is the MHPG concentration determined to be attributable to the brain, and is useful as a determination of the NE activity of the brain of a human subject.

Considering the procedure in more detail, the first step is to establish the normal level of MHPG and VMA in the body. There is a wide variation between individuals, requiring that a body level be established for each patient. There are also fluxuations over a period of time in the MHPG and VMA levels of a specific individual due to variations in activity, food digestion, etc. It has been found that an individual's total body level of MHPG may vary by as much as 270% over a period of time. It is believed that this results partially from the fact that NE is metabolized in muscle tissue and stored in fat. However, the brain's level and metabolism of NE is believed to be relatively constant, being affected to a significant extent only by the individual's relative state of awareness. Although a measurement from a single sample may be helpful, several samples should be taken over a period of time to achieve accuracy by smoothing out the effects of a momentary rise or fall of body levels of MHPG and VMA levels. The number of samples and the period between them should be large enough for accuracy but not so large as to be overly expensive or inconvenient.

A minimum and maximum time period for collection would be between about four and forty-eight hours with a preferable period being about twenty-four hours. At least three samples should be taken, but more than ten would not add substantially to accuracy. Five to seven samples would be preferable.

MHPG and VMA may be measured from either blood or urine, but their concentration in blood is only about 0.001 of that found in urine. While blood samples may be more susceptible to an accurately timed collection schedule, the very low concentrations of MHPG and VMA make accurate measurement very difficult. Accordingly, urine samples are preferred even though there are problems of regularity and quantity of collection.

After the initial measurements of MHPG and VMA, the patient is given an intravenous dosage of labelled NE. Because of the dangers associated with radioactive labels, non-radioactive isotopes are preferred, the least expensive and easiest to use being deuterium.

The quantity of labelled NE ($NE_d$) administered should be large enough to be measurable when metabolized to VMA and MHPG, but small enough so as to not interfere with the body's normal NE reaction rates. It is anticipated that the method of this invention may successfully be employed using about 0.12 mg of labelled NE. The NE injection is preferably administered over a period of time. Two hours at a rate of 1.0 $\mu$g/minute might be optimal.

After the $NE_d$ injection, blood or urine samples will again be taken. The frequency and number of samples taken after the $NE_d$ injection preferably should be the same as the pre-injection samples, but taking several samples over a period is more important for the post-injection collections since the peak concentrations of labelled VMA and MHPG will usually occur at different times. Due to the fact that NE is absorbed into body tissues, and to allow the NE time to metabolize, it may be desirable to wait for a period of one-half to twelve hours before beginning the post-injection collections.

The actual measurement of the MHPG and VMA in the samples is a multi-step process involving, in the case of deuterated compounds, a gas chromatograph mass spectrometer (GCMS). First, the pre- and post-injection samples are separately pooled and aliquots are removed from the pools. Then, a calibration standard is added and the MHPG and VMA will be extracted from the aliquots. Each of the four vials now present (pre-injection MHPG, post-injection MHPG, pre-injection VMA, and post-injection VMA, each with a standard) are then separately reacted with trifluoroaceticanhydride (TFAA) or pentafluoropropionanhydride (PFPA) to produce a fluoro derivative. A fluoro derivative is preferred over the unreacted molecule because of the tendency of the unreacted molecule to form hydrogen bonds which broaden the peak produced by the measuring instrument. FIG. 2 is a representation of MHPG reacting with TFAA. VMA undergoes a corresponding reaction.

Typically, the standard will be the same as the fluorated compound being measured, except that it will have a different number of deuterium atoms in its structure, although an entirely different molecule may be used. The ratio of the relative abundances of the sample and the standard are used to calculate the concentration or mass of the sample.

The extraction of MHPG and VMA from the urine is itself a complex procedure. After the pre- and post-injection samples are separately pooled, an aliquot (1.0 to 10.0 ml) will be removed from one of the pools and mixed with a known quantity of internal standard. For example, to measure pre-injection MHPG ($MHPG_{d0}$), 10.0 ml is removed from the pre-injection pool and is mixed with 2.0 ml of 2,5,6,7-D-MHPG ($MHPG_{d3}$) of a known concentration.

Isotopes such as $MHPG_{d3}$ may be purchased commercially or prepared in the laboratory. In either case, it would be desirable to test the isotopic purity of the compound. This test may be performed by a GCMS comparison of the compound with a known concentration of another isotope, using techniques well known to those skilled in the art.

Commercial sources of the isotopes include Merk and Co., St. Louis, Mo. and Merk, Sharp and Dohme, Point Claier Dorval, Quebec, Canada.

Laboratory preparations may be prepared as follows:
For 2,5,6-d-VMA:
1. Dissolve 50.0 mg VMA in 1.0 ml $D_2O$.
2. Add 2.0 ml concentrated DCl.
3. Reflux at 190° C. until solution turns pink or rosy red.
4. Analyze for purity.
5. The $VMA_{d3}$ is dried down and stored in a freezer.

For 2,5,6-d-MHPG:
1. Prepare 2,5,6-d-VMA as above.
2. React with borane methyl sulfide (BMS).

The extraction may then proceed as follows:
1. Add 2.0 ml of glucouronidase and 1.0 ml of acetate buffer (pH 6.2) to the urine aliquot. Place the mixture in a 37° C. water bath and allow to stand overnight (12 hours). This step converts MHPG glucuronide and MHPG sulfate to uncombined MHPG.
2. Saturate the solution with $Na_2SO_4$ and then add 5.0 ml of ethyl acetate. Cap and shake for three minutes.
3. Draw off most of the organic layer and place it in a centrifuge tube.
4. Add 50.0 ml of ethyl acetate to the aqueous phase and shake for five minutes. Draw off the organic layer and add it to the previously collected organic layer.
5. Place the tube containing the organic fluid into a 37° C. water bath and take the fluid to dryness with nitrogen gas.
6. Add 100 $\mu$l of ethyl acetate and 100 $\mu$l of TFAA. Cap tightly and let react for one hour at room temperature.
7. Dry gently with nitrogen gas and reconstitute with 10 $\mu$l of ethyl acetate.
8. Inject 1 $\mu$l into a GCMS.

The VMA is prepared for injection in a similar manner except that a deuterated VMA standard is used and the VMA is reacted with anhydrous methanol for twenty minutes prior to the reaction with TFAA.

After the $MHPG_{d0}$ and $MHPG_{d3}$ have been injected into the GCMS, the instrument will sense the two compounds and report their relative molecular abundance in unitless numbers. The relationship between the numbers produced by the GCMS and the concentrations of the MHPG samples may be expressed, $$\frac{V_{d0} \cdot C_{d0}}{V_{d3} \cdot C_{d3}} = 1/k \frac{A_{d0}}{A_{d3}}. \quad [2.]$$

This may be rewritten as, $$C_{d0} = 1/k \frac{A_{d0} V_{d3} C_{d3}}{A_{d3} V_{d0}}, \quad [3.]$$

where $V_{d0}$ is the volume of the urine aliquot, $C_{d0}$ is the concentration of $MHPG_{d0}$ in the urine aliquot, and $A_{d0}$ is the relative abundance of $MHPG_{d0}$ as measured by the GCMS. The sub-d3 variables are those for the $MHPG_{d3}$ standard added to the urine aliquot. The value of $C_{d3}$ is determined by the technician when it is mixed into solution. For example, 0.01 g of 100% isotopically pure MHPG diluted into 2 ml would give $C_{d3}$ a value of 0.005 g/ml. The constant, k, may be theoretically necessary because the slope of $A_{d0}/A_{d3}$ plotted against $(V_{d0} \cdot C_{d0})/V_{d3} \cdot C_{d3}$ is not necessarily equal to unity. The value of k may be easily found for a particular instrument and isotope combination as follows. Prepare an $MHPG_{d0}$ and $MHPG_{d3}$ mixture of known mass ratio (mass (M) = concentration (C) times volume (V). The value of k is then given by the equation, $$k = \frac{\frac{A_{d0}}{A_{d3}}}{\frac{M_{d0}}{M_{d3}}}, \quad [4]$$

where $A_{d0}$ is the relative abundance of $MHPG_{d0}$ as measured by the GCMS and $M_{d0}$ is the mass of $MHPG_{d0}$ in the mixture. The sub-d3 variables represent those for $MHPG_{d3}$.

While k may be of theoretical importance, in practice its significance diminishes. Referring to equation 1, it may be seen that each side of the equation reduces to identical units (usually of either mass or concentration). Thus, the constant k will appear on both sides of the equation and will cancel.

After the VMA and MHPG measurements have been obtained (usually in units of weight of product/volume of sample), they will be applied in the following equation:

$$MHPG_{(brain)} = MHPG_{(total)} - \left[ VMA_{(total)} \left( \frac{MHPG_d}{VMA_d} \right) \right]. \quad [1.]$$

Since for all practical purposes, all VMA is produced by the periphery, the right side of the equation may be written as, $$MHPG_{(total)} - \left[ VMA_{(periphery)} \left( \frac{MHPG_d}{VMA_d} \right) \right]. \quad [5.]$$

The fraction $MHPG_d/VMA_d$ represents the ratio of MHPG to VMA produced by all the NE in the periphery. Multiplying the quantity of VMA in the periphery $[VMA_{(periphery)}]$ by this ratio gives the quantity of MHPG in the periphery $[MHPG_{(periphery)}]$. Substituting in the equation, the MHPG contribution of the brain can now be determined as follows.

$$MHPG_{(brain)} = MHPG_{(total)} - MHPG_{(periphery)} \quad [6.]$$

As an example, the total urine from a human subject is collected over a twenty-four hour period, beginning at 10 PM on day 1, just prior to the subject's sleep. At 10 PM on day 2, a two-hour intravenous injection containing 0.12 mg of 2,5,6,7-D-norepinephrine is administered to the subject. After a ten-hour wait, at 8 AM on day 3, a second twenty-four hour total urine collection is begun. The pre-injection samples are pooled and the post-injection samples are pooled. The total volume of each pool is recorded. The MHPG and VMA are then separately extracted from the samples, using the techniques described above, and taking measures to assure that the pre- and post-injection samples are treated identically. Taking first, for example, the pre-injection MHPG, after the addition of a calibration standard, the extraction, and reaction with TFAA, the dried compound is diluted with 10. $\mu l$ of ethyl acetate and 1.0 $\mu l$ is injected into a GCMS. The following hypothetical information is now known:

| k | 1 |
|---|---|
| $A_{d0}$ | 33542. |
| $A_{d3}$ | 60781. |
| $V_{d0}$ | 1.00 ml |
| $V_{d3}$ | 1.00 ml |
| $C_{d3}$ | 0.002 mg/ml |

$A_{d0}$ and $A_{d3}$ are the GCMS relative values for the molecular abundance of $MHPG_{d0}$ and $MHPG_{d3}$, respectively, and are obtained directly from the apparatus. $V_{d0}$ is the volume of the urine aliquot and $V_{d3}$ is the volume of the MHPG standard added to the aliquot. $C_{d3}$ is the concentration of the $MHPG_{d3}$ standard and is determined by the technician when the $MHPG_{d3}$ solution is prepared. Applying these figures to equation 3, we find that $C_{d0}$, the concentration of $MHPG_{d0}$ in the urine aliquot, is 0.00110 mg/ml. Similar measurements will be made for the other three variables of equation 1 and a value for $MHPG_{(brain)}$ will be obtained.

Thus, the method above can be used to determine the MHPG produced by the brain of a human which can be correlated to the NE activity of the brain. Such information can be useful in diagnosing abnormalities in NE concentrations and hence in treating affective disorders. Furthermore, such information can be correlated with the results of treatment of depressive disorders by the administration of anti-depressant drugs to provide insights as to the neuropharmacological action of such drugs and valuable diagnostic information on the effective dosage of the drugs.

The disclosed procedures may be used to trace compounds other than NE, VMA, and MHPG. For instance, three different analyses may be performed after injection of labelled Dopamine (DA). DA, which is itself a precursor of NE, metabolizes to VMA (through NE), 3,4-dihydroxyphenylacetric acid (DOPAC), homovanillic acid (HVA), and 3-methoxy-4-hydroxyphenylethanol (MHPE). For these compounds, the following equations, which correspond to equation 1, may be used.

$$DOPAC_{(brain)} = DOPAC_{(total)} - \left[ VMA_{(total)} \left( \frac{DOPAC_d}{VMA_d} \right) \right] \quad [1a.]$$

$$HVA_{(brain)} = HVA_{(total)} - \left[ VMA_{(total)} \left( \frac{HVA_d}{VMA_d} \right) \right] \quad [1b.]$$

$$MHPE_{(brain)} = MHPE_{(total)} - \left[ VMA_{(total)} \left( \frac{MHPE_d}{VMA_d} \right) \right] \quad [1c.]$$

For a more accurate determination of the brain's DA activity, the above equations may be summed to give, $$[DOPAC_{(brain)} + HVA_{(brain)} + MHPE_{(brain)}] = \quad [1d.]$$

$$[DOPAC_{(total)} + HVA_{(total)} + MHPE_{(total)}] -$$

$$\left[ VMA \times \left( \frac{DOPAC_d + HVA_d + MHPE_d}{VMA_d} \right) \right]$$

In the above equations 1a, 1b, 1c, and 1d, as with equation 1, VMA is the metabolite which is produced substantially entirely in the periphery and the other metabolite is produced in both the brain and the periphery. This method is equally adaptable for use in studying other biochemical pathways involving the blood-brain barrier.

There is a possibility that one of the precursors of a metabolite which is being studied can cross the blood-brain barrier. In establishing clinical evaluation standards, this should produce no problem since the same degree of error will be present in every measurement. In theoretical studies, however, the extent of cross-over may be determined by radioactive studies on animals.

It may be possible to eliminate the pre-injection samples and determine that data by summing the values of the labelled and unlabelled metabolilites from the post-injection samples. For instance, if $NE_d$ is injected and MHPE and VMA are measured, the sum of he post-injection levels of labelled and unlabelled MHPG should equal the pre-injection level of MHPG. Comparative studies should quickly indicate the relative impact the injected precursor has on metabolite levels.

Radioactive NE may be substituted for deuterated NE. Such a substitution may have advantages when working with laboratory animals. For example, it would be possible to administer smaller does of diagnostic NE and to take smaller samples of body fluids. Metabolite levels could be easily measured without need of extraction from the body fluids. Other uses and applications of the method above can be made without departing from the scope of the invention as set forth in the following claims.

What is claimed is:

1. A method for obtaining an indication of the brain norepinephrine activity of a human subject, comprising:
   a first step of collecting first body fluid samples for measuring therefrom the body levels of 3-methoxy-4-hydroxyphenylglycol and vanillylmandelic acid;
   a second step of intravenously injecting a non-radioactive isotope-labelled norepinephrine into the peripheral nervous system;
   a third step of collecting second body fluid samples for measuring therefrom the levels of heavy isotope labelled 3-methoxy-4-hydroxyphenylglycol and vanillylmandelic acid;
   a fourth step of determining the relative concentrations of heavy isotope-labelled 3-methoxy-4-hydroxyphenylglycol and of heavy isotope-labelled vanillylmandelic acid from said second samples and preparing a ratio of the relative concentrations from said determinations that indicates the relative degree of conversion of norepinephrine into 3-methoxy-4-hydroxyphenylglycol and into vanillylmandelic acid in the peripheral nervous system; and
   a fifth step of using the ratio and the measured body level of vanillylmandelic acid from said first sample to determine the contribution of 3-methoxy-4-hydroxyphenylglycol from the peripheral nervous system, and obtaining an indication of the brain's norepinephrine activity by deducting the 3-methoxy-4-hydroxyphenylglycol of the peripheral nervous system from the measured body level of 3-methoxy-4-hydroxyphenylglycol of the first sample.

2. The method of claim 1 wherein the body fluid samples of said first step and said second step are fluids from the class consisting of blood and urine.

3. The method of claim 2 wherein the collections of said first and third steps each additionally comprise the taking of from three to ten samples over a period of from about four to about twenty-four hours.

4. The method of claim 1 wherein the labelled and unlabelled 3-methoxy-4-hydroxyphenylglycol and vanillylmandelic acid from the collections of said first step and said third step are reacted with a compound from the group consisting of trifluoroaceticanhydride and pentafluoropropionanhydride, and the reacted material is examined with a mass spectrometer in measurement of the labelled and unlabelled material.

5. A method for determining the amount of 3-methoxy-4-hydroxyphenylglycol produced by the brain separately from that produced by periphery, comprising:
   a step of sample collection for measuring the body levels of 3-methoxy-4-hydroxyphenylglycol and vanillylmandelic acid;
   a step of administering to the body a dose of isotopically labelled norepinephrine;
   a step, subsequent to said norepinephrine administration step, of sample collection for measuring the body levels of isotopically labelled 3-methoxy-4-hydroxyphenylglycol and vanillylmandelic acid; and
   a step of calculating the brain's contribution of 3-methoxy-4-hydroxyphenylglycol.

6. The method of claim 5 wherein said step of sample collection for measuring the body level of 3-methoxy-4-hydroxyphenylglycol and vanillylmandelic acid takes place prior to said step of administering norepinephrine.

7. The method of claim 5 wherein the dosage of labelled norepinephrine is small compared to the normal body level of norepinephrine and said step of sample collection for measuring the body level of 3-methoxy-4-hydroxyphenylglycol and vanillylmandelic acid takes place simultaneously or subsequent to said step of administering norepinephrine.

8. The method of claim 5 wherein the isotopically labelled norepinephrine comprises a deuterated norepinephrine isotope.

9. The method of claim 5 wherein the steps of measuring the unlabelled and the isotopically labelled 3-methoxy-4-hydroxyphenylglycol and vanillylmandelic acid comprise reacting the compounds with trifluoroaceticanhydride, adding a measured quantity of a known standard, and with the aid of an instrument, comparing the relative amounts of the chemical to be measured and the standard.

10. A method for measuring the brain contribution of a biochemical first product separately from the peripheral contribution of the first product where the first product is capable of passing the blood-brain barrier but one or more specific precursors of the first product are not capable of passing the blood-brain barrier, and where a second product of one or more of the precursors, the second product not being in the chain of reaction of the first product, is formed to a measurably significant extent only in the periphery, comprising:
measuring the concentration of the first product and of the second product;
administering an isotopically labelled dose of the common precursor;
measuring the concentration of the resulting isotopically labelled first product and second product; and
calculating the brain contribution of the first product from the data of said measuring steps.

11. The method of claim 10 wherein said calculating step includes manipulation of the data according to the equation $$P1_b = P1_{b+p} - \left[ P2_p \left( \frac{P1_d}{P2_d} \right) \right]$$

where $P1_b$ is the brain contribution of the first product, $P1_{b+p}$ is the measured total brain and peripheral contribution of the first product, $P2_p$ is the measured peripheral contribution of the second product, $P1_d$ is the measured amount of isotopically labelled first product and $P2_d$ is the measured amount of isotopically labelled second product.

12. The method of claims 10 or 11 wherein the first product is a metabolite of norepinephrine and is also from the class consisting of precursors of 3-methoxy-4-hydroxyphenylglycol, metabolites of 3-methoxy-4-hydroxyphenylglycol and 3-methoxy-4-hydroxyphenylglycol.

13. The method of claims 10 or 11 wherein the second product is a metabolite of norepinephrine and is also from the class consisting of precursors of vanillylmandelic acid, metabolites of vanillylmandelic acid, and vanillylmandelic acid.

14. The method of claims 10 or 11 wherein the first product is a metabolite of norepinephrine and is also from the class consisting of precursors of 3-methoxy-4-hydroxyphenylglycol, metabolites of 3-methoxy-4-hydroxyphenylglycol and 3-methoxy-4-hydroxyphenylglycol, and the second product is a metabolite of norepinephrine and is also from the class consisting of precursors of vanillylmandelic acid, metabolites of vanillylmandelic acid, and vanillylmandelic acid.

15. The method of claims 10 and 11 wherein the first product is 3-methoxy-4-hydroxyphenylglycol and the second product is vanillylmandelic acid.

16. The method of claims 10 or 11 wherein the injected precursor comprises isotopically labelled norepinephrine.

17. The method of claims 10 or 11 wherein the injected precursor comprises isotopically labelled dopamine.

18. The method of claim 17 wherein the second product comprises homovanillic acid.

* * * * *

UNITED STATES PATENT AND TRADEMARK OFFICE
CERTIFICATE OF CORRECTION

PATENT NO. : 4,259,947
DATED : April 7, 1981
INVENTOR(S) : Peter C. Kobrinsky

It is certified that error appears in the above-identified patent and that said Letters Patent are hereby corrected as shown below:

Col. 1, line 12, delete "+" and insert therefor --35--.

Col. 4, line 27, delete "M̄erk" and insert therefor --Merck--; line 28, delete "Merk" and insert therefor --Merck--; line 29, delete "Claier" and insert therefor --Claire--.

Col. 6, amend the table between lines 25 and 35 to show k and its corresponding value 1 as part of the data in the table rather than appearing to be headings for two columns as follows:

$$\begin{aligned}
--A_{d0} & \quad 33542. \\
A_{d3} & \quad 60781. \\
V_{d0} & \quad 1.00 \text{ ml} \\
V_{d3} & \quad 1.00 \text{ ml} \\
C_{d3} & \quad 0.002 \text{ mg/ml} \\
k & \quad 1 --.
\end{aligned}$$

Col. 7, line 39, delete "metabolilites" and insert therefor --metabolites--; line 41, delete "MPHE" and insert therefor --MHPG--; and line 41 delete "he" and insert therefor --the--.

Signed and Sealed this

Twenty-second Day of September 1981

[SEAL]

Attest:

GERALD J. MOSSINGHOFF

*Attesting Officer*     *Commissioner of Patents and Trademarks*